(12) United States Patent
Steadman Booker et al.

(10) Patent No.: US 12,279,900 B2
(45) Date of Patent: Apr. 22, 2025

(54) USER INTERFACE FOR X-RAY TUBE-DETECTOR ALIGNMENT

(71) Applicant: KONINKLIJKE PHILIPS N.V., Eindhoven (NL)

(72) Inventors: Roger Steadman Booker, Aachen (DE); Walter Ruetten, Linnich (DE); Matthias Simon, Aachen (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 4 days.

(21) Appl. No.: 17/642,413

(22) PCT Filed: Jul. 5, 2021

(86) PCT No.: PCT/EP2021/068432
§ 371 (c)(1),
(2) Date: Mar. 11, 2022

(87) PCT Pub. No.: WO2022/008397
PCT Pub. Date: Jan. 13, 2022

(65) Prior Publication Data
US 2023/0117579 A1    Apr. 20, 2023

(30) Foreign Application Priority Data

Jul. 7, 2020  (EP) .................................... 20184465

(51) Int. Cl.
*A61B 6/00* (2024.01)
*A61B 6/08* (2006.01)
(Continued)

(52) U.S. Cl.
CPC .............. *A61B 6/4441* (2013.01); *A61B 6/08* (2013.01); *A61B 6/4291* (2013.01);
(Continued)

(58) Field of Classification Search
CPC ................ A61B 6/4291; A61B 6/4405; A61B 6/4441; A61B 6/4452; A61B 6/461; A61B 6/587;
(Continued)

(56) References Cited

U.S. PATENT DOCUMENTS

| | | |
|---|---|---|
| 7,997,799 B2 | 8/2011 | Jabri |
| 8,535,337 B2 | 9/2013 | Chang |

(Continued)

FOREIGN PATENT DOCUMENTS

| | | |
|---|---|---|
| EP | 3235430 A1 | 10/2017 |
| JP | 2013123629 A | 6/2013 |
| WO | WO2008023301 A2 | 2/2008 |

OTHER PUBLICATIONS

PCT International Search Report, International application No. PCT/EP2021/068432, Sep. 30, 2021.
(Continued)

*Primary Examiner* — Dani Fox
*Assistant Examiner* — Soorena Kefayati
(74) *Attorney, Agent, or Firm* — Larry Liberchuk

(57) ABSTRACT

System (SYS) for supporting X-ray imaging and related methods. The system (SYS) comprises a machine learning module (MLM), a logic (LG) configured to compute output correction information for adjusting an imaging geometry of an X-ray imaging apparatus to achieve a target imaging geometry. A modulator (MOD,L-MOD, H-MOD, S-MOD) is the system is configured to provide a user instruction for imaging geometry adjustment. The user instruction is modulated based on the output correction information. The machine learning module was previously trained on training data including a specific user's responses to previous instructions.

10 Claims, 9 Drawing Sheets

(51) Int. Cl.
*A61B 6/42* (2024.01)
*A61B 6/58* (2024.01)

(52) U.S. Cl.
CPC ............ *A61B 6/4405* (2013.01); *A61B 6/582* (2013.01); *A61B 6/587* (2013.01); *A61B 6/588* (2013.01)

(58) Field of Classification Search
CPC ........... A61B 6/545; A61B 6/08; A61B 6/582; A61B 6/488
See application file for complete search history.

(56) References Cited

U.S. PATENT DOCUMENTS

| | | | |
|---|---|---|---|
| 9,649,074 | B2 | 5/2017 | Simon |
| 10,136,864 | B2 * | 11/2018 | Maack .................. A61B 6/545 |
| 10,531,850 | B2 | 1/2020 | Tkaczyk |
| 10,542,958 | B2 | 1/2020 | Merckx |
| 10,653,385 | B2 | 5/2020 | Mehendale |
| 2007/0109294 | A1 * | 5/2007 | Gotman ................ G16H 30/40 345/418 |
| 2014/0341349 | A1 * | 11/2014 | Lalena ................. A61B 6/587 378/62 |
| 2014/0376700 | A1 * | 12/2014 | Kwak .................. A61B 6/587 378/205 |
| 2015/0049863 | A1 * | 2/2015 | Stagnitto ............... A61B 6/587 378/205 |
| 2015/0374314 | A1 * | 12/2015 | Maack .................. A61B 6/587 378/151 |
| 2016/0074003 | A1 * | 3/2016 | Manke ................ A61B 6/4405 378/206 |
| 2016/0302747 | A1 * | 10/2016 | Averbuch ............ A61B 6/5235 |
| 2017/0100089 | A1 * | 4/2017 | Chang ................. A61B 6/0492 |
| 2018/0061045 | A1 * | 3/2018 | Profio .................... A61B 6/032 |
| 2018/0092613 | A1 * | 4/2018 | Ancar .................. A61B 6/487 |
| 2018/0092619 | A1 * | 4/2018 | Gu ......................... A61B 6/465 |
| 2018/0296178 | A1 * | 10/2018 | Chang ....................... G06T 7/73 |
| 2018/0338742 | A1 * | 11/2018 | Singh ................... A61B 6/587 |
| 2019/0015067 | A1 * | 1/2019 | Gorges ................. A61B 6/581 |
| 2019/0059827 | A1 * | 2/2019 | Nye .................... A61B 6/4035 |
| 2019/0069871 | A1 * | 3/2019 | Tkaczyk .............. A61B 6/4452 |
| 2019/0282194 | A1 * | 9/2019 | Tkaczyk ............... A61B 6/542 |
| 2019/0380668 | A1 * | 12/2019 | Richard ................ A61B 6/488 |
| 2020/0085385 | A1 * | 3/2020 | Nye ...................... A61B 6/032 |
| 2020/0258222 | A1 * | 8/2020 | Bernhardt ............ A61B 6/4441 |
| 2021/0059626 | A1 * | 3/2021 | Qi .......................... G06T 7/0012 |
| 2021/0212650 | A1 * | 7/2021 | Wang ................... G06V 10/98 |

OTHER PUBLICATIONS

Mitchell T.M. et al., "Well-Posed Learning Problems", Machine Learning, p. 2, section 1.1, McGraw-Hill, 1997.

* cited by examiner

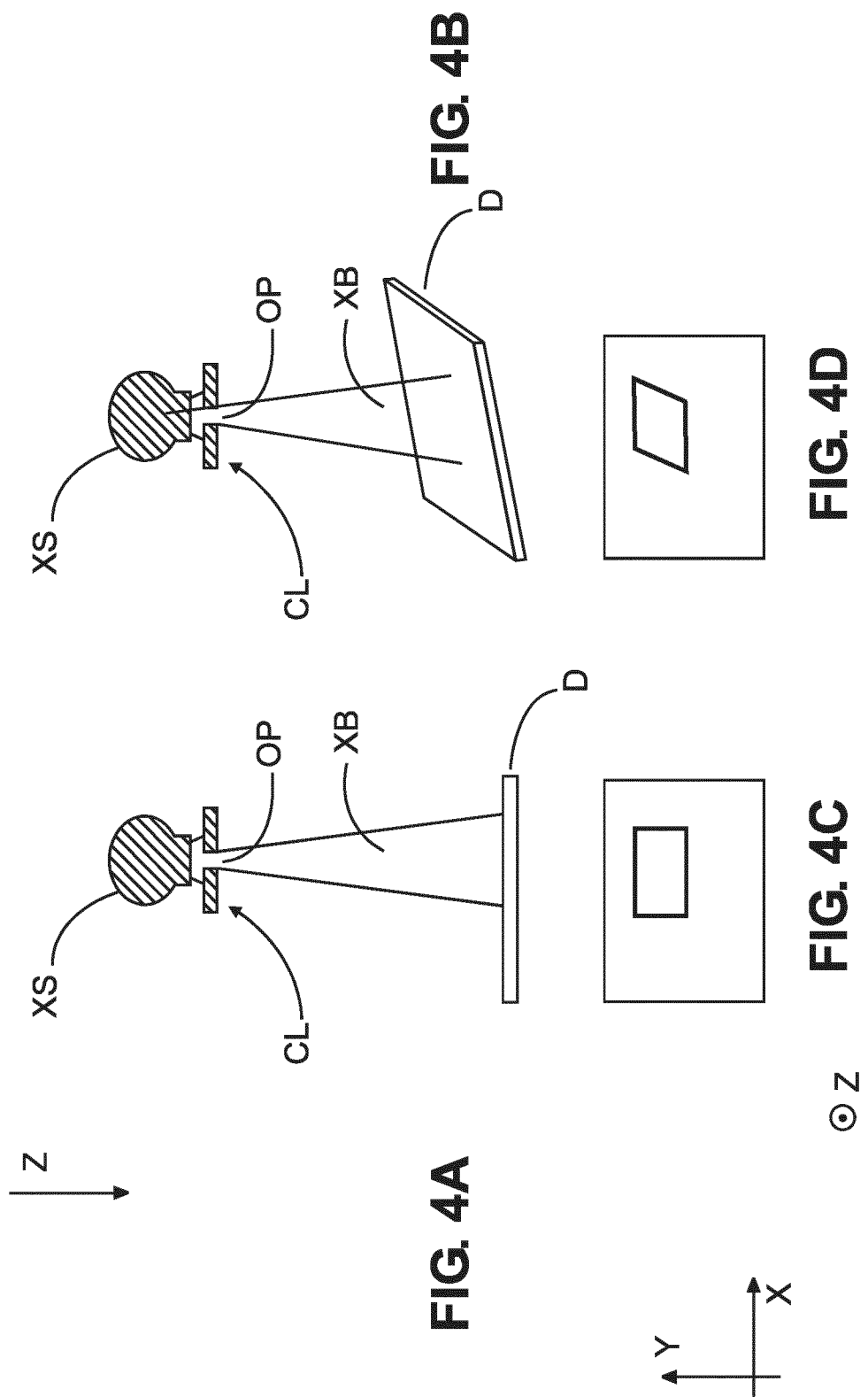

USER INTERFACE FOR X-RAY TUBE-DETECTOR ALIGNMENT

FIELD OF THE INVENTION

The present invention relates to a system for supporting X-ray imaging, to an arrangement including an X-ray imaging apparatus and such a system, to a method for supporting X-ray imaging, to a computer program element and to a computer readable medium.

BACKGROUND OF THE INVENTION

Medical personnel sometimes use mobile X-ray imagers. They allow acquisition of X-ray images even under awkward, adverse conditions. For example, elderly patients in care homes who have been bed-ridden for long will need to have a chest X-ray taken regularly to monitor for possible build-up of water in their lungs which could lead to pneumonia.

It has been noted however that, although some of those mobile X-ray imagers are equipped with devices (such as collimators) to help keep dosage down, X-ray dosages for patients and personnel were still surprisingly high. In addition, image throughput on occasion fell below expectations.

A mobile X-ray imager is described in Applicant's WO2008/023301.

U.S. Pat. No. 10,136,864 B2 discloses an X-ray apparatus for image acquisition and a related method. The apparatus comprises a field-of-view corrector (CS) configured to receive a scout image (SI) acquired by the imager with a tentative collimator setting in a pre-shot imaging phase.

SUMMARY OF THE INVENTION

There may therefore be a need for improved mobile X-ray imaging.

The object of the present invention is solved by the subject matter of the independent claims where further embodiments are incorporated in the dependent claims. It should be noted that the following described aspect of the invention equally applies to the said arrangement including the X-ray imaging apparatus, to the method for supporting X-ray imaging, to the computer program element and to the computer readable medium.

According to a first aspect of the invention there is provided a system for supporting X-ray imaging, comprising:

a pre-trained or trainable machine learning module, configured to compute output correction information for adjusting an imaging geometry of an X-ray imaging apparatus, wherein the imaging apparatus is of the mobile type comprising an X-ray source and an X-ray detector with no rigid mechanical coupling between the X-ray source and the X-ray detector, to achieve a target imaging geometry, and a modulator configured to provide a user instruction for the imaging geometry adjustment, modulated based on the output correction information, the machine learning module previously trained on training data including a specific user's responses to previous user instructions for imaging geometry adjustments.

In other words: the machine learning module computes personalised correction information accounting for the manner in which a specific user tends to adjust the imaging geometry.

In embodiments, the system further comprises a memory storing multiple pre-trained or trainable machine learning models associated with different users.

In embodiments, the system further comprises a user identification functionality configured to identify a user based on a credential and to cause selection of the machine learning module from said multiple pre-trained or trainable machine learning models based on the said credential.

In embodiments, one any, any two, or all there of the following modulators are envisaged:

i) the modulator is configured to control a visible light projector to project a light beam onto a surface, the light beam modulated in accordance with the said output correction information and/or ii) the modulator is configured to control a haptic vibrator to impart on a) a manual actuator mechanically coupled to an X-ray source of the imaging apparatus or b) on an electrical input device communicatively coupled to the X-ray source of the imaging apparatus, mechanical vibrations in accordance with the said output correction information, and/or iii) the modulator is configured to control an electroacoustic transducer to sound out instructions in accordance with the said output correction information.

In embodiments, upon a change of a current imaging geometry the user instruction is updated. For example, the light beam causing the pattern and/or the imparted vibrations and/or the sound is modulated accordingly. In this manner, a dynamic system is provided with feedback as the user changes the imaging geometry.

In embodiments, the light based modulation by the modulator includes any one or more of a change of a light pattern cast by the light beam, a change in light gradient, a change in light color and/or hue.

In embodiments, the surface is in an examination region of the imaging apparatus. The surface may a contour surface of the patient, but may be any other suitable surface, such as portion of the patient support (table, bed) or any other suitable equipment.

In embodiments, the surface is defined by a patient when present in the examination region.

In embodiments, the navigation unit configured to compute input correction information based on which the output correction information is computed by the machine learning module, the input correction information computed based on any one of more of: i) sensor readings provided by sensors arranged at the imaging apparatus; ii) a scout image acquired using a collimator setting to effect a projection being detected at a detector of the imaging apparatus the projection having a shape, the correction information being computed based on a distortion of the shape relative to a pre-determined reference shape, iii) an intensity profile as detected at the detector and caused by an anti-scatter grid.

In another aspect there is provided an arrangement including the system as per any one of the above described embodiments, and the imaging apparatus.

In another aspect there is provided a method for supporting X-ray imaging, comprising:

computing, by a machine learning module, output correction information for adjusting an imaging geometry of an X-ray imaging apparatus wherein the imaging apparatus is of the mobile type comprising an X-ray source and an X-ray detector with no rigid mechanical coupling between the X-ray source and the X-ray detector, to achieve a target imaging geometry, and providing, by a modulator, a user instruction for imaging geometry adjustment, modulated based on the output correction information, wherein the machine learning module is previously trained on training data including a specific user's responses to previous user instructions for imaging geometry adjustments.

The proposed system allows addressing in particular the issue of high dose in mobile X-ray. In mobile X-ray, the source and the detector are separate components not rigidly coupled. There is no defined and known fixed spatial relationship between the two. This can cause difficulties in adjusting for the correct imaging geometry, such as alignment, centration, source-detector distance SID, etc. Time pressured personnel may be led into a loop of repeated retakes until a useful diagnostic frame can be captured. This comes at a dose and time cost. The proposed system allows adjusting for the correct imaging geometry quickly and accurately. The system uses machine learning to provide instructions tailored to the particular manner in which a given user reacts to imaging geometry adjustment instructions. Fewer retakes and fewer adjustment iterations may be needed with the proposed machine learning based system. The system is trained on training data collected in a monitoring phase where the user executed adjustments versus the actually provided set of instructions is recorded. From this training data, better instructions, tailored to user habits, are learned by adjusting parameters of the machine learning module to fit the training data in previous training. Once trained, the pre-trained machine learning model can be used to predict the said tailored correction information and hence instructions to quickly guide the user to correct imaging geometry.

In yet another aspect there is provided a computer program element, which, when being executed by at least one processing unit, is adapted to cause the processing unit to perform the method as per any one of the above mentioned embodiments.

In another aspect still, there is provided a computer readable medium having stored thereon the program element.

Definitions

"user" relates to a person, such as medical personnel or other, operating the imaging apparatus or overseeing the imaging procedure. In other words, the user is in general not the patient who is imaged.

In general, the "machine learning component" is a computerized arrangement that implements a machine learning ("ML") algorithm and ML model that is configured to perform a task. In an ML algorithm, task performance improves measurably after having provided the arrangement with more training data to process. The performance may be measured by objective tests when feeding the system with test data. The performance may be defined in terms of a certain error rate to be achieved for the given test data. See for example, T. M Mitchell, "Machine Learning", page 2, section 1.1, McGraw-Hill, 1997.

BRIEF DESCRIPTION OF THE DRAWINGS

FIGS. 4A-D show examples of different imaging geometries determinable by using a collimator;

DETAILED DESCRIPTION OF EMBODIMENTS

Figure 1B:
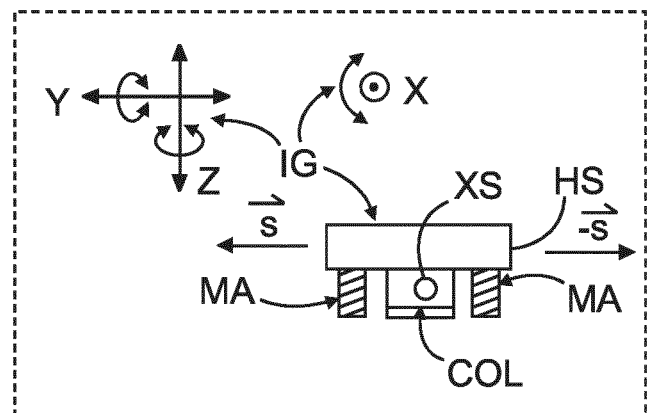
FIGS. 1A, B show an imaging arrangement including a mobile X-ray imaging apparatus.
Figure 1A:
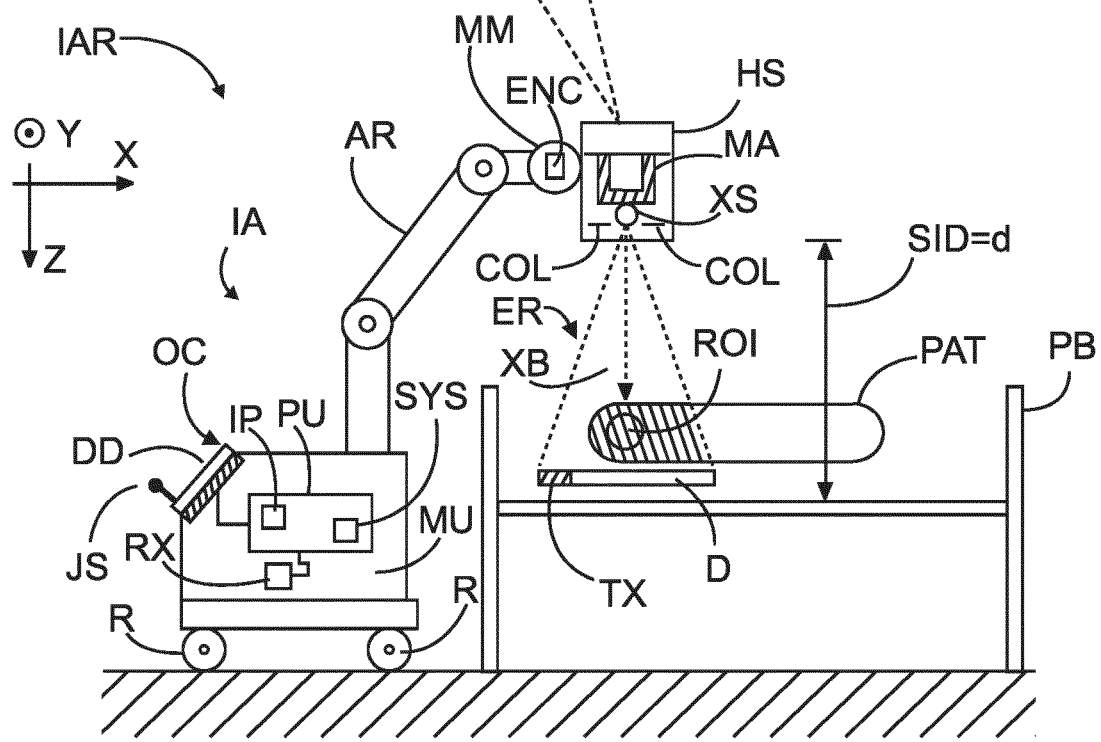

With reference to FIG. 1A there is shown a mobile X-ray apparatus IA. Such or similar mobile X-ray apparatuses may be used in intensive care wards (ICU) or in hospital emergency departments, A&Es, or in regular wards, etc. They may also be used outside hospitals, such as by ambulance staff when attending emergency sites.

According to one embodiment, the X-ray imaging apparatus IA ("imager") is of the "dolly type" and comprises a main unit MU on rollers R so as to be position-able at a convenient location relative to the patient PAT. The main unit MU may include a power source such as a battery and/or a mains connection. Patient PAT may stand, sit or may be lying on hospital patient bed PB or on an ambulance stretcher or cot. Being wheel mounted is however not a necessity herein. Instead, the imager may be arranged as a portable device in a carrier case for instance, so can be readily deployed off-site, outdoors, etc.

The imager includes an X-ray source XS capable of generating an X-ray beam XB for imaging at least a region of interest ROI of a patient PAT. The imager further includes a portable X-ray detector D to register X-radiation. Ideally, the ROI resides in an examination region ER between the source XS and the detector D. Optionally the imager may include a collimator COL to collimate radiation beam XB in shape and/or cross-section area as egressing from said source XS. In more detail, during an image acquisition, the X-ray beam XB emanates from X-ray tube XS, passes through patient PAT at said region ROI, experiences attenuation by interaction with matter therein, and the so attenuated beam XB then strikes detector D's radiation sensitive surface. The radiation sensitive surface is made up of a plurality of detector cells also referred to as (detector) pixels. The cells respond to exposure to the (attenuated) X-ray beam XB by issuing a corresponding electric signal. The collection of said signals is then translated by a data acquisition system ("DAS"—not shown) into a respective digital values representative of said attenuation for a given cell. The collection of values can be converted into a projection image by an image processor IP. Image contrast in attenuation-based projection imaging may be conferred by different attenuation capability of different tissue types. However, the present disclosure is not confined to attenuation based imaging, as other modalities such as phase-contrast imaging is also envisaged herein in embodiments.

The imager IA may include an operator console OC for clinical personnel (in the following referred to as operator or user) to operate the imager IA. For example, user USR may control via said console OC image acquisition by activating the source XS to trigger X-ray exposures. The console OC may also include a display unit DD for viewing the acquired X-ray projection image, or for displaying a user interface to assist user in operating the mobile X-ray apparatus IA, etc.

The mobile or portable detector unit D is in embodiments of the flat panel type, so is arranged as a relatively flat, slab or plate-like object. In an example, detector unit D is rectangular in shape, measuring for example about 30 cm×40 cm with a thickness of about 3-5 cm or less.

The detector D may be capable of communicating with the X-ray apparatus operating console OC via wireless connection. The console and the mobile detector include suitable wireless interfaces, such as an emitter TX at the detector D, and a receiver RX at the console. Image signals can thus be transferred to a computing device PU integrated at the main unit MU where the above described image processing may take place. Alternatively, the image processing takes place in a central computer remote from the imaging site. The imagery may then be forwarded to mobile computing device, such as smart phone, tablet, laptop, etc of the user. In this case, the imager is of the "bare bone" type, with on-site equipment essentially comprising only the X-ray source, the operating console, and a suitable holder/positioning mechanism AR,MM as will be explained in more detail below. Although less convenient for most cases, wired embodiment can be envisaged where the detector D communicates via wired socket connection with main unit.

Exactly which detector cells are exposed to the imaging beam XB, and hence can ultimately contribute to image formation, is a matter of adjusting for the correct imaging geometry. The imaging geometry determines amongst others the field of view (FOV) for any imaging session. A correct imaging geometry adjustment calls for i) correct tube XS—detector D alignment, ii) correct source XS-detector D distance (SID), iii) correct collimator aperture. FOV adjustments are challenging with mobile X-ray imagers as will now be illustrated in more detail with reference to a clinical user scenario.

In one use scenario, the user USR would position the mobile X-ray imager IA via its rollers R close to patient PAT's bed PB for example. The patient is then asked to sit up or, if to infirm to do so, is gently rolled over by medical care staff and detector plate D is positioned on the bed's B support surface. The portable detector unit D may include a handle or similar to facilitate its positioning. The patient PAT is then rolled back or asked to lie down so as to cover essentially with their chest or back, or other regions of interest ROI, the portable detector D. To make this experience more convenient for the patient the mobile detector may include heating elements arranged across its surface so as to ensure said surface is essentially close to body temperature when the patient PAT's body contacts the detector D surface when lying down. One possible clinical application is chest X-ray, but imaging other ROIs are also envisaged herein, such as the abdomen, arm, leg, etc.

As can be appreciated from the above scenario, and in particular in the chest X-ray scenario, large parts (or even the whole) of the X-ray detector D's radiation sensitive surface is visually occluded during the imaging because the patient is lying on it. Detectors come in various size. A rather compactly built detector may completely "vanish" out of sight when a patient is asked to lie down on same.

In other words, if the user USR were to proceed with the actual image acquisition after a rough-an-quick X-ray tube-patient alignment, there is a serious risk of obtaining sub optimal images because the detector and X-ray tube/detector and collimator are likely to be misaligned for example.

In order to carry out imaging geometry adjustments, imager IA may include a number of mechanisms. For example, the mobile X-ray apparatus may include one or more X-ray source XS positioning and/or pose adjustment mechanisms MM, AR. Said mechanism(s) allow(s) position and/or pose control in 3D of the X-ray tube XR relative to the detector D.

FIG. 1B is a schematic illustration in frontal view of the imaging apparatus's source as housed in housing HS. A mounting mechanism MM of the source XS supports adjustments by angulation around any one of up to three spatial axis X,Y,Z and/or shifts, shown as an exemplary shift vector $\vec{s}$. The mounting mechanism MM may include sliders, ball-bearing units with rollers, wheels rails etc. to enable shifts and/or rotations.

According to one embodiment the X-ray source XS positioning and/or pose adjustment mechanism may further include arm AR, with mounting mechanism MM coupled to its distal end. Optionally, the arm AR is articulated to add further degrees of freedom to position the tube XS in space. For example, the articulated arm may allow advancing the tube XS away from the main unit MU, towards where the detector D happens to be located. The mounting mechanism allows changing pose/position of the tube relative to the arm AR. Thus, the arm AR may be operated for a coarse positioning over the detector whilst independent operation of the mounting mechanism MM allows for refining the position and/or pose. The arm, AR thanks to its one or more articulations, may allow adjustment for SID vertically. Optionally, the arm AR may be telescopic to facilitate SID adjustments. Alternatively still, the mounting mechanism MM may be slidable along arm AR which may be arranged as an upright pole. Adjustment of the SID allows controlling magnification. Any of the above mentioned adjustments may be done manually by a suitable manual actuator MA, or by operation of a electro-mechanical actuator through remote control by a user input device JS, such as a joystick or similar.

For example, X-ray source XS is arranged in a housing HS. The housing is coupled to the mounting mechanism MM. As shown in FIG. 1, the housing HS may include one or more manual actuators MA, such as one or more of hand wheels, levers, handles etc. for the user to engage with the adjustment mechanism MM and hence manually adjust the tube XR pose and/or position in space. Alternatively or additionally, at least partly motorized embodiments are also envisaged in which there are arranged a number of suitable electro-mechanical actuators (not shown) such as stepper motors or the like via which shift/rotation with respective to axis X,Y,Z can be independently effected. The user input device, such as the joystick JS or similar may be provided at the console OC to allow the user to remotely control tube XS position and/or pose and/or the SID. Collimator blades (not shown) of the collimator may be operable by actuators to adjust the collimator aperture to decrease or increase the beam XB shape and/or cross-sectional area. This allows further controlling the FOV, in addition to shifting the source XS by operation of mounting mechanism MM.

The mounting mechanism MM of the X-ray source XS that affords the change of pose and/or position may include encoders ENC which allow tracking the current position/angulations. Similar encoders may be provided for the articulated arm AR, and/or for the collimator COL blades.

Whilst position and/or pose control in 3D is desirable, nothing herein exclude simpler imagers IA with restricted degrees of freedom. For example, in some such embodiments, the source XS can only be shifted in a plane with no rotations for example.

The danger of adjusting for a wrong imaging geometry, for example misalignment, is aggravated by the mobile nature of the imager IA as there is no permanent, pre-defined and a priori known spatial relationship between X-ray tube/collimator and the detector's image plane as would be the case, for example, in a C-arm imager where detector, collimator and X-ray tube are permanently/rigidly mounted in opposed relationship on the respective ends of the C-arm. If the FOV is incorrect, clinically essential portions may be cut-out. Retakes may be necessary which in turn increases patient dose and time costs.

As will be gathered from the above, a correct mutual spatial constellation between the X-ray source XS and the detector D is important for good image quality. To this end, the imaging arrangement IAR includes a computerized system SYS to assist the user to achieve this correct mutual spatial constellation. The said spatial constellation is referred to herein as the imaging geometry. In other words, the imaging geometry defines the spatial relationship between the following four imaging participants: detector D, X-ray source XS, the X-ray beam XB, and the region of the patient one wishes image, the ROI.

The computerized system SYS may be integrated in a computing unit PU of the imaging apparatus AI. Alternatively, the system is administered by two or more processing units in a Cloud or distributed architecture setup such as on servers, etc., suitably connected in a communication network with the imager IA. The system SYS, referred to herein as the "user guidance system", may be implemented in hardware, in software or partly in both. The computerized system SYS takes the "guess work" out of image acquisition with mobile X-ray. The computerized module SYS guides the user to adjust for correct imaging geometry quickly and accurately at very low or even no dosage cost.

Figure 2A:
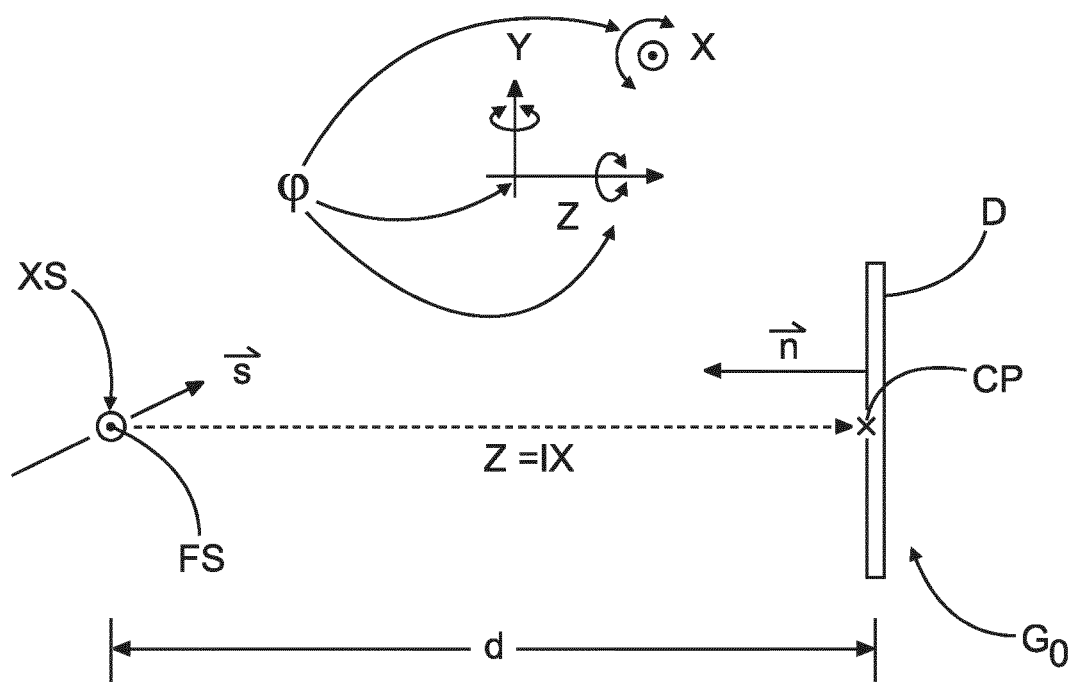
FIGS. 2A, B are schematic drawings illustrating imaging geometries.

Reference is now made to FIGS. 2A, B which explore in more detail the concept of imaging geometry and also introduces certain terminology which will be used herein. Referring first to FIG. 2A, an imaging geometry IG includes among others centration, angulation and distance SID=d. In more detail, a desirable or correct imaging geometry is achieved if the source XS is properly centered relative to the detector D. This centration can be described by means of the imaging axis IX, that is, an imaginary line that one may run from the focal spot FS of the tube XS to a center point CP on the radiation sensitive surface of the detector D. In embodiments, for instance, the detector surface is a rectangular or square shaped area and the center point is where the two diagonals cross. When properly centered, the imaging axis is parallel to the normal vector $\vec{n}$ of the radiation sensitive surface of the detector D. In order to adjust a current imaging geometry Gj for the target imaging geometry, $G_0$, in which the source XS and the detector are centrally aligned, a shift or translation $\vec{s}$ and/or an angulation (p may be required. Angulation (p is indicated in the top part of FIG. 2A which may involve one, two or three respective rotations about three spatial axes X,Y,Z. The rotations are referred to herein respectively as pitch, roll and yaw. In addition to shift S and angulation φ, an adjustment of the distance d between the X-ray source and the detector may be required. The said distance d is also referred to as the source to image distance "SID". The SID determines the magnification and the angulation/centration the FOV. It will be understood that the above translation S and angulations (p or rotation are indicated relative to a world co-ordinate X'Y'Z' or to a local co-ordinate system X,Y,Z that passes through the focal spot FS of the source XS as shown in FIG. 2A. In general, and with continuing reference to FIG. 2A, degrees of freedom for changing the imaging geometry may be conceptualized as an affine transformation $\mathcal{T}$. Each affine can be formalized as a composition of rotation $\mathcal{R}$ and a lineal shift (translation) $\mathcal{S}$ or vice versa:

$$\mathcal{T}: \mathcal{R}\,a?? \mathcal{S} \text{ or } \mathcal{S}\,a?? \mathcal{R} \tag{1}$$

Figure 2B:
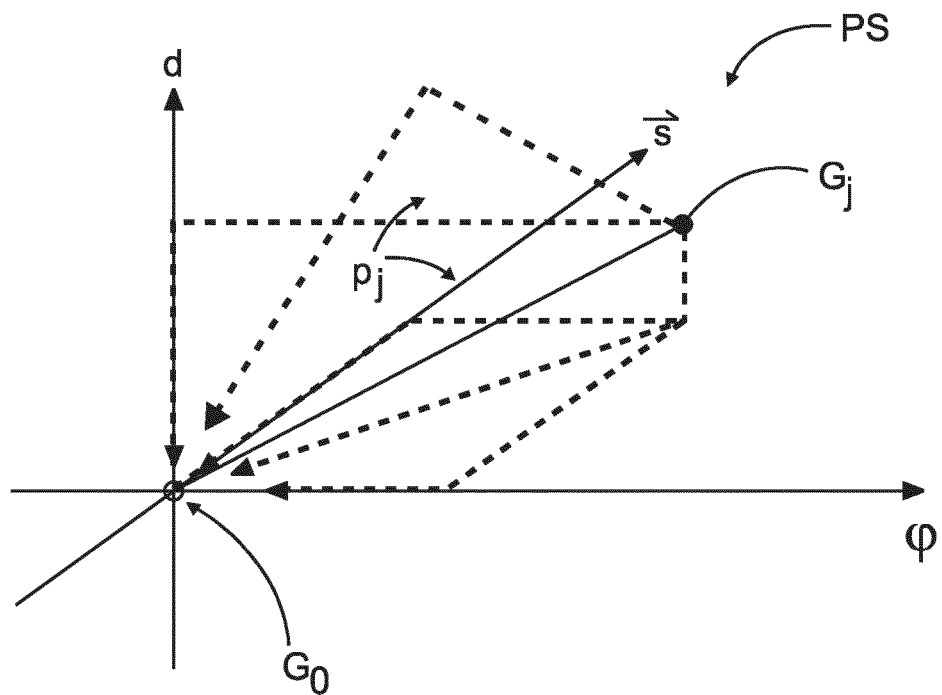

Transformation $\mathcal{T}$ acts on imaging geometries. An imaging geometry can be described as a point in a seven dimensional space with three spatial co-ordinates for the shift vector S, three angular co-ordinates for the angulation φ (which each component describing the rotation around the respective axis X,Y,Z) and distance d. The coordinates represent a point in a vector space, referred to as phase space PS, of which a simplified 3-dimensional representation is shown in FIG. 2B. The correct centrally aligned imaging geometry $G_0$ is shown at the origin of phase space and $G_j$ represents an off-center and/or misaligned geometry $G_j$, possibly not at the correct distance d.

A correction from current imaging geometry to target imaging geometry may be conceptualized as correctional information, represented as a vector in this phase space extending from point $G_j$ to the origin, with target imaging geometry $G_0$ represented, without loss of generality, by the origin. The correction information may be represented as the Euclidean distance or more generally as the component-wise difference vector between the vectors for imaging geometry points $G_0,G_j$. If $G_0$ is at the origin, correction information are the components of the vector of $G_j$.

Figure 3:
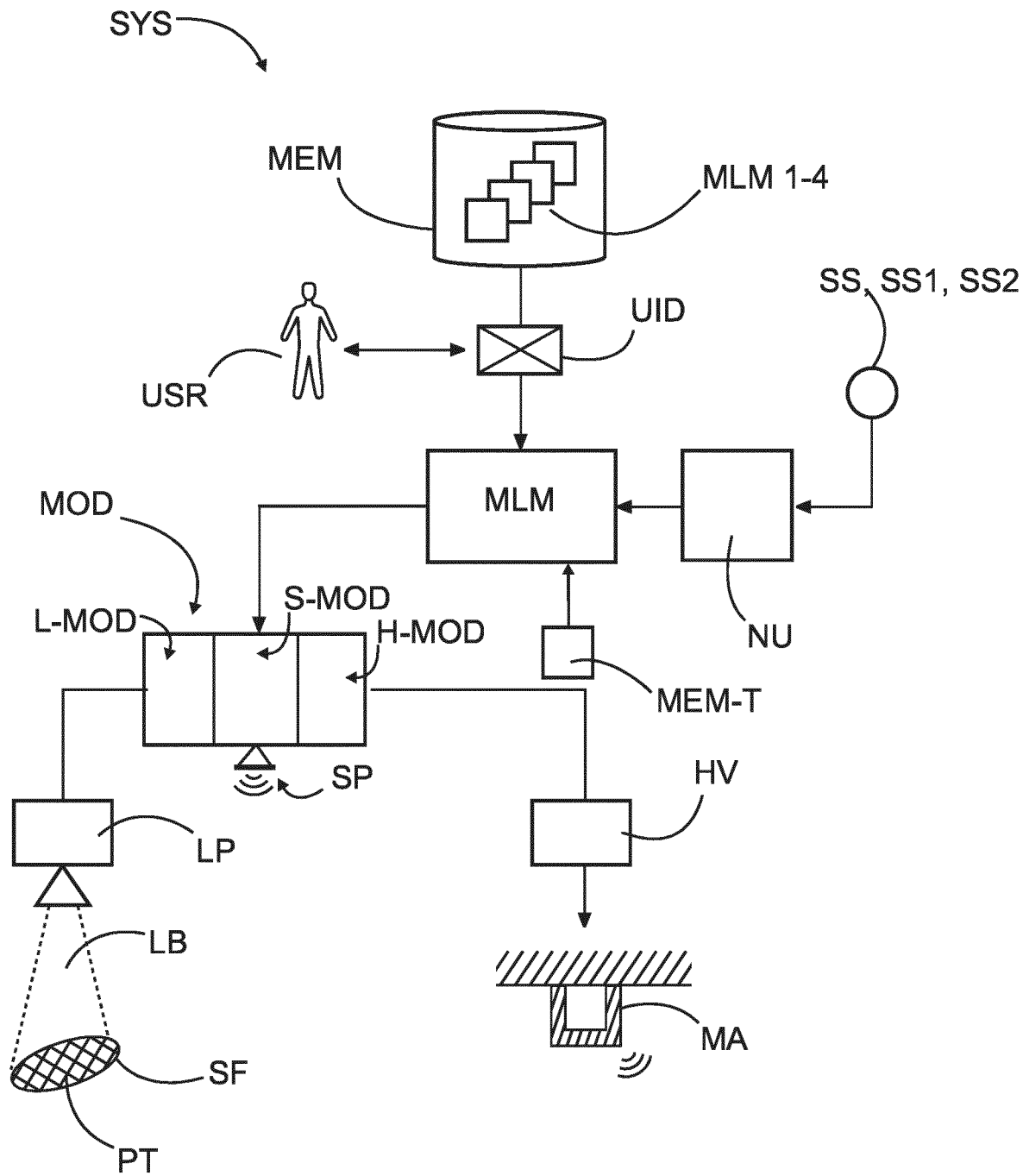
FIG. 3 shows a block diagram of a machine learning based system to support X-ray imaging by a user.

The imaging geometry adjustment itself can be achieved in multiple ways by realizing different correction paths $p_j$ in phase space PS as shown in dashed arrows in FIG. 2B. For example, one may first perform a shift along S and then change the angulation φ or vice versa. Furthermore, each angulation may be performed as composition of multiple partial rotations $\varphi = \varphi_1\,a??\,\varphi_2, a?? \ldots, a?? \varphi_m$, and the same holds true for the shift $\vec{s} = \vec{s}_1\,a?? \vec{s}_2 a?? \ldots, o\ \vec{s}_k$. There are a multitude of correction paths $p_j$ that each represent respective correction information on how to modify the current geometry $G_j$ for the centralized and aligned target imaging geometry $G_0$. The user guidance SYS as envisaged herein is configured to facilitate image geometry adjustment by user USR. The guidance SYS shown in a schematic block diagram in FIG. 3 to which reference is now made. The system SYS includes a machine learning module MLM that incorporates a machine learning model M. The machine learning model M has been previously trained based on training data. The training operation will be explained more fully below. The system SYS is thus operable in three modes: a monitoring mode in which training data is recorded, a training mode in which the model is trained based on the recorded training data, and deployment mode in which the now trained model is used.

Assuming for a moment that the machine learning model has been sufficiently trained, the machine learning module is configured to assist the user to achieve swift imaging geometry adjustment prior to imaging.

Broadly, a navigation unit NU of the system establishes a first version of correction information, representable as a certain correction path $p_j$ in phase space as in FIG. 2B. The machine learning module processes the correctional information provided by the navigation unit and computes personalized correction information which may be turned into instructions for the user USR as will be explored more fully below.

Embodiments for the navigation unit NU are envisaged herein and will be discussed in more detail first before moving on to the machine learning module. In embodiments, but not necessarily in all embodiments, one or more sensors SS are used that provide measurement data which are processed by the navigation unit NU to compute the first correct information. The machine learning module MLM computes therefrom the personalized correction information as output. The personalized correction information as computed by the machine learning module accounts for the manner in which the specific user tends to adjust the imaging geometry.

The output personalized correction information is then processed by a modulator MOD to modulate the personalized computed correction information into user instructions, sensory expressions which can be interpreted easily by the user so that they can adjust, for instance by engaging with the manual actuator MA, the imaging geometry to achieve the target imaging geometry $G_0$. Referring back to phase space on FIG. 2B, a standard correction path $p_0$ provided by the navigation unit NU is transformed into a preferred path $p_j$ that corresponds to the manner in which a given user USR tends to adjust imaging geometry as learned from previous adjustments as encoded in the training data. The machine learning module does not simply map to a fixed correction paths, but has learned user's habits as they tended to respond to past instructions.

In one embodiment the modulator MOD is a light modulator L-MOD that modulates visible light emitted by a light projector LP. The light projector is instructed by the light modulator to cause a light beam LB being projected on a suitable surface SF. The light beam is modulated into a light pattern PT that encodes the personalized instructions as computed by the machine learning module MLM. The light projector LP may be advantageously integrated into the housing HS of the X-ray source XS. It can be used to project the light beam LB, and hence the pattern PT, on a surface portion formed by the patient's skin or clothing (e.g. gown) worn by the patent, etc. Using light by the light projector LP modulated in this manner is particularly advantageous in adverse low visibility light conditions.

In addition, or instead of such light modulations, a haptic modulator H-MOD may be used. The haptic modulator H-MOD is operable to encode the personalized correction information as provided by the machine learning module MLM into personalized instructions in form of vibration patterns PT by controlling a haptic vibrator HV. The haptic vibrator HV may be integrated for example into handles MA of the source housing HS for example or into the hand portion of the joystick By changing frequency and/or intensity the vibrations, user USR can thus be guided to the target geometry $G_0$.

In general, the modulated signal that represents the (personalized) instruction varies with distance in phase space of the current imaging geometry G from the target imaging geometry $G_0$. For instance, referring to the haptic vibrator HV, this may be caused to vibrate with higher intensity or frequency, the more the current imaging geometry deviates from the target geometry $G_0$, and in turn may lessen in intensity/or frequency as target imaging geometry $G_0$ is approached, with vibration ceasing once target imaging geometry is assumed. Similarly, real-time feedback modulation by the light modulator L-MOD may be in terms of changing the light intensity with distance from current imaging geometry $G_j$ to target imaging geometry $G_0$. In addition or instead, a light color or a pattern of light colors may change. For instance a red color indicative of a bad imaging geometry may dynamically transition into a green color for instance that indicates that the target image geometry is being approached. Optionally, a hue of a given color or brightness may be changed as configurable. In another example embodiment, a tilt or rotation may be indicated with a color gradient, e.g. from red to blue. The operator can thus manipulate the source angulation and tilt until a homogeneous color pattern is achieved. Specifically and in embodiments, the light pattern itself may be made up of different portions, each coding for different spatial aspects of the required geometry adjustments. For example, a portion in a red color indicates the source XS is too close to one edge of the detector, whilst another portion in a blue color indicates the source XS is too far from another edge. The spatial arrangement of the portions of the pattern correlate to locations of the respective edges. Thus, this type of light modulated instructions support the user in source XS centration, eventually achieving equal distance from source XS to both detector edges. If the source XS is centered but if source-detector distance is not correct, e.g. too small, both portions of the pattern will be rendered red. And if source-detector distance is too large, both portions are rendered blue. Correct source-detector distance d and centration may be indicated by both portions of the light pattern transitioning into a homogenous target color, such as a green color. In a similar manner "Up/down" deviations in respect to the other two detector edges can be can be indicated by color changes of another pair of light pattern portions. The projected light pattern may cover an area in a shape similar to the detector's radiation sensitive surface such as square or rectangle. The four portions are formed at the four edges of the area, in spatial correlation with the four detector edges. In general, the light modulation can be any one more of a varying light color, color gradient, hue or intensity. The light instructions vary with distance in phase space PS of current geometry $G_j$ to target geometry $G_0$. Similar for the haptic embodiments. The above described light modulation pattern allows for efficient user-machine feedback. It helps illuminate the ROI and helps focus user. It furthermore consolidates different spatial aspects of the instruction (centration, SID adjustment) into a single light pattern, thus facilitating quick imaging geometry adjustments.

In addition or instead, suggestive animations or still graphics may be projected onto the surface SF such as on the patient. For example, arrows that appear to move in the direction of the corrective shift may be displayed, or curly arrows that show the amount and orientation by apparently winding around the respective graphic rendition of the rotation axes may be so projected.

In embodiments, there is a sound modulator S-MOD that is coupled to and drives an electroacoustic transducer SP, such as a loudspeaker, to sound out instructions. The instructions may be in natural language or in other sound pattern. For example, a sound pitch may vary as the user adjusts the imaging geometry to approach the target imaging geometry. Any of the above described modulators S-MOD, L-MOD, H-MOD may be used as standalone without the other two, or all three may be combined. Any sub-combination of any two of the three modulators S-MOD, L-MOD; H-MOD are also envisaged herein.

The machine learning module MLM in combination with the modulator MOD, either light or haptic based, should be understood to operate in real time feed-back mode. In other words, any adjustment by the user USR of the current imaging geometry is picked up by the navigation unit NU. The navigation unit NU re-computes new correction information which is fed into the machine learning module MLM to provide updated personalized correction information. The new personalized correction information is passed on to the modulator MOD to re-modulate the output signal to cause new/updated personalized instructions in form of updated light or vibration signal patterns.

Instead of, or in addition to the above described embodiments of haptic and optical light pattern modulation to encode the user instructions, other embodiments of the modulator MOD are also envisaged. For example, the modulator MOD may include a graphics driver to control the display device DD at the console OC. The instructions may be displayed on the display device DD of the operator console OC for instance, or on any other monitor communicatively coupled to the output system SYS. The instructions may be displayed in textual, alphanumeric form or as still or animated graphics.

In the following operation of the navigation unit NU is now being described in more detail. The navigation unit NU may be arranged in software, in hardware or partly in both, and may preferably be integrated in the system SYS. As mentioned above, the navigation unit may compute the first (input) correction information based on measurements received from certain sensors SS, to be provided as input to the machine learning module MLM.

One or more such sensors SS may be used. In embodiments, at least two sensors are used, one arranged at the detector D and the other at the X-ray source, for instance at its housing HS. In embodiments, the respective pair of sensors includes gyroscopic and/or acceleration sensors but any other suitable sensor technology may be used. As the detector is substantially stationary when placed behind the patient, for instance when the patient lies on the same, sensors SS1 at the detector (referred to herein as "detector sensor") are expected to provide stable measurements that can be compared to current measurements of the sensor SS2 attached at the X-ray source (referred to herein as the "source sensor"). Whilst the user is adjusting the imaging geometry by rotation and/or translation of the X-ray source, the source sensor measurements are compared to the fixed measurement of the detector sensor to establish the correction information. The gyroscopic and/or acceleration sensors adjustment of angulation, but not necessarily centering. To achieve centering, the sensors SS may further comprise a combination of i) one or more electromagnetic field generating units ("EFGU"), such as a coils, and ii) an electromagnetic field sensor ("EFS"), such as hall sensor, coils or other. The EFGU and the EFS are attached to tube XS and detector D, respectively, or vice versa.

In some imaging protocols, patient PAT is asked to sit in an almost upright position, which may require that the source to be tilted at angle other than 0° or 90°. To this end, the above mentioned use of gyroscopic and/or accelerometer sensors arranged (e.g. integrated) into both the detector D and X-ray tube XS may be advantageous to adjust for the correct imaging geometry.

However, use of such external sensor circuitry SS is not necessary in all embodiments herein, where existing imaging components may be used instead to establish the correction information. In one such embodiment, X-ray detector projection imagery is recorded in response to low dose exposures, referred to herein as pre-shots, in combination with collimator COL control. The principle is explained in more detail with reference to FIGS. 4A-D. FIGS. 4A,C represent a situation where the beam XB is off center whilst FIGS. 4B,D represents a situation where additionally the imaging axis is at an angle or tilted relative to the normal $\vec{n}$ of the detector D surface. Each of these cases of bad imaging geometries can be established by way of projection scout imagery as shown in FIGS. 4C,D. The scout images can be obtained by exposure to a low dose beam by adjusting tube voltage and/or tube current accordingly. Preferably, tube voltage is maintained and the current is lowered. The low dose beam is collimated into a pre-defined and known shape such as a rectangular shape or any other pre-defined shape. It is therefore a priori known how the projected shape recordable as projection imagery is supposed to look like. If the shape, as registered at the detector, deviates from the pre-defined shape, this is an indication for an incorrect imaging geometry such as a tilt and/or off-center situation as exemplary shown in FIGS. 4C,D. For example in FIG. 4C, projection footprint in the shape of the small rectangle can be obtained by threshold-segmentation. Its center point is established. The projection footprint center point is compared with a the priori known center point location of the detector surface and the vector difference between the two can be correlated to shift vector $\vec{s}$ by which the source needs to be shifted in order to achieve centration. Similarly, in the projection footprint in FIG. 4D, this is a distortion of the expected rectangular shape into a parallelogram. The angles of the parallelogram can be measured by segmentation for the edges of the footprint, and correlated by 3D geometry techniques to the tilt currently experienced by the X-ray source relative to normal of the detector surface. Again, this information can be correlated to the angular correction φ as required for a correction for the target imaging geometry $G_0$. In either case of FIGS. 4C,D, the correlation is based on principles of classical affine geometry in 3D space and the laws of projections.

Figure 5A:
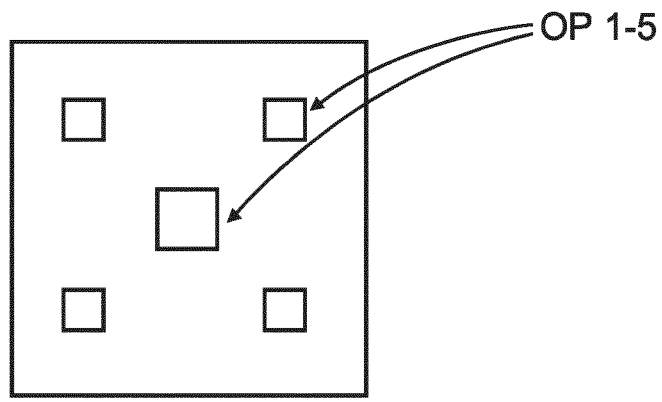
FIGS. 5-C show collimator masks that may be used in embodiments to establish a mismatch between a current imagery and a target imaging geometry.
Figure 5B:
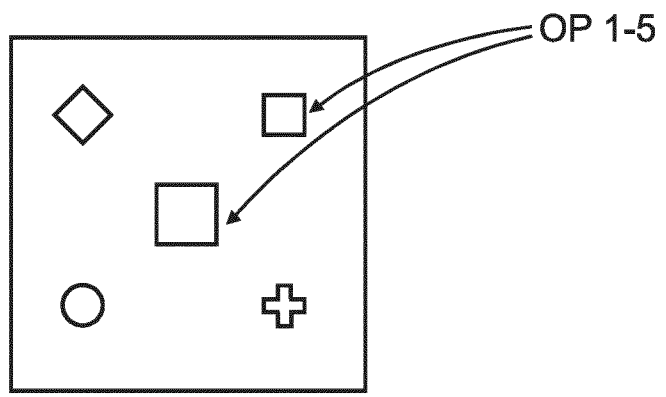
Figure 5C:
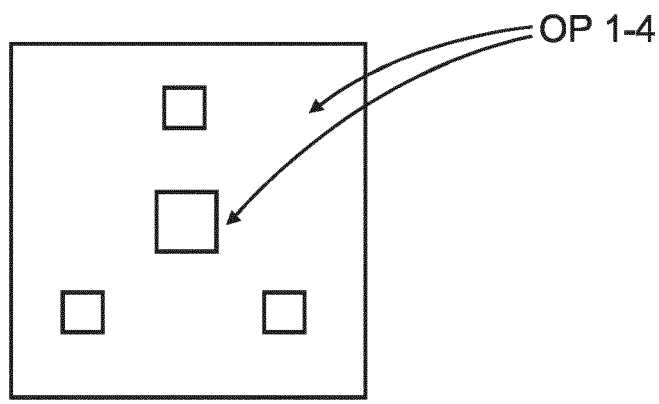

FIGS. 5A-C show further embodiments of collimator based correction information computation. In these embodiment, collimator masks are used that can be swung into the pre-shot X-ray beam by a revolving mechanism or other. The mask includes a pre-defined number of openings OP1-5 or apertures. Whilst 5 are shown, this is exemplary and there can be more or less. The apertures OP1-5 have pre-defined shapes and the respective geometry of the projection footprints caused by each of the openings can be used as explained above in FIG. 4 to compute the amount of correction information required to establish the target imaging geometry. To reduce ambiguity in respect to the correction information, the shapes may differ, for instance, for each of the plurality of openings OP1-5 may have a different shape from any other so all openings differ, although this may not be necessarily so in all embodiments where merely two or three openings with differing shapes may suffice. The number of shapes are preferably cut into the mask in a triangular layout arranged as three vertices of an imaginary triangle as shown in FIG. 5C. Alternatively, as shown in FIG. 5B, the layout is that of a center point and the four vertices of an imaginary square or rectangle. Again, using an odd number of apertures and/or laying them out in non-symmetric fashion may help reduce above mentioned ambiguity. Instead of or in addition to using different shapes as in FIG. 5B, apertures OP1-5 of different sizes are used as exemplary shown in FIG. 5A. Again, because, size, shape and distortion of the projection footprints recordable are pre-determined by the apertures OP1-5. If there is deviation, correction information may be computed based on principles of affine geometry. The projection footprints in FIG. 5A resembles footprints of pencil beams w (in this example 5)

which provide preferably all necessary information to correct for distance, tilts and rotations errors of the detector D relative to the source XS. The collimator settings in FIGS. 5A (and B) help reduce radiation dose. FIG. 5A shows a symmetric arrangement. Non-symmetric projection footprint patterns, for example with distinctive shapers e.g. round, rhomboid, cross, etc. are also envisaged as in FIG. 5B. It will be understood however, that the shapes and layouts ins FIGS. 5A,B are exemplary and not limiting.

The area size of the collimated scout image may be established along both spatial directions of the detector plane. The ratio r therewith to the total area detector D surface may be established by the navigation unit NU. This ratio can be used to establish the correct SID. More specifically, to compute the SID the collimator projection footprint is compared with extensions of the scout image. Given a FCD (focus-collimator distance), the SID=FCD*r.

In the collimator-based embodiments of the navigation unit NU, an imaging session proceeds in two consecutive phases: a pre-shot phase and in a subsequent image acquisition phase. In the pre-shot phase the scout image s is acquired where the X-ray radiation tube operates at a much lower dosage, for example 5% of the actual dosage needed for the instant patient PAT under examination. The scout image may be very small, typically in the region of 50%-80% of the whole detector surface area. In one embodiment, the dimension of the scout image are 50% of detector D's extension in one spatial-direction and 50% of detector D's extension in the other spatial -direction, resulting in 25% of the detector D's area. The percentages are merely for illustration and by example and are not to be construed as limiting the present disclosure. The image size reduction is achieved by a suitable collimation aperture when acquiring the pre-shot scout image. For control purposes and to further assist in imaging geometry adjustments, the pre-shot images may be displayed on the display device. Once correction information is computed and correct imaging geometry has been adjusted for, the image acquisition may commence with a repeat exposure, this time at a higher diagnostic dose to acquire a diagnostic image. The image may be displayed on the display device DD.

The collimated scout image can be used to compute not only the SID, but also required angular tilt and/or rotation. Image processing in detector D circuitry may average (or bin) over detector pixels to larger image units, e.g. comprising 5×5 or 10×10 native detector pixels. By this averaging into larger super-pixels, the signal to noise ratio of the recorded scout image shape versus background noise is enhanced at the expense of a small uncertainty in position. Depending on the desired alignment accuracy, the area of the super pixel could be e.g. 2 mm×2 mm or 3 mm×3 mm etc. In addition, the use of a small collimator setting further reduces the dose to the patient. By suitable binning, the dose to be expended on the scout image may be reduced to about 1/20-1/10 of the diagnostic dose.

In a further embodiment still the imaging apparatus includes an anti-scatter grid ASG and this harnessed for imaging geometry adjustment purposes as will now be explained in more detail.

The anti-scatter grid ASG is used to block out secondary radiation that is caused by Compton scattering as the primary radiation passes through the patient. Secondary, or scatter radiation, compromises image quality. In order to minimize the amount of secondary radiation impinging on the detector cell surface an anti-scatter grid ASG is positioned between patient and detector surface. According to one embodiment the grid is either permanently installed on top of the detector surface or is removable. A removable anti-scatter grid ASG may for example be snap-fitted onto the mobile detector via a number of pins. According to one embodiment the detector and/or the grid ASG may include detection means in order to detect whether there is an anti-scatter grid mounted. In embodiments, the anti-scatter grid ASG is essentially a grid-like structure formed from small fins extending away from and approximately perpendicular to detector surface, pointing towards the X-ray source XS. The grid when mounted covers essentially all the detector surface. The layout of the fins may be 1D in which case the fins are approximately parallel or 2D in which there are two sets of fins crossing each other.

In the event the anti-scatter grid ASG is mounted on the detector D, the projected image of the ASG grid ("projected focal spot") may be used for imaging geometry corrections. If the detector is not fully aligned, the ASG casts shadows on the pixels modulating the intensity of the impinging X-ray beam. This intensity profile can be analyzed by image processing by the navigation unit NU to establish correction information. For 2D ASG particularly, a perfectly parallel detector with a wrong SID (off focus) will cause a circular gradient intensity profile to be detected at detector D. Deviations from such a profile, e.g. detection of elongated ellipsoid profile, are indicative of off-center shifts, tilts and rotation errors. That is, the geometry of the projected focal spot can be used to determine the correction information. In order to fully specify angulation adjustments, additional correction information may be required such as the collimator COL induced information as discussed above at FIG. 5, or other.

Turning now to the machine leaning module MLM, operation of this may be motivated as follows. If it was not for the proposed user guided system SYS, it may be understood that conventionally provided user instructions for adjusting imaging geometry may require iterative application of such adjustments, rather than a single such application. This may be longwinded. For instance, the user may react on instructions to over-shoot the target geometry or fall short thereof. For instance, even explicit instructions that inform the user to turn the source by for example 500 counter-clockwise or similar may result in the user overshooting this target and by turning the source by say 600 instead. The user will then be informed to turn source XS back by 10° back, and so forth, etc. until the target geometry is considered established (within a suitable allowance margin). The manner in which users react to the provided instructions is a matter of personal depositions. For instance, more impatient users tend to over-shoot the target whereas more timid users may tend to fall short of the required correction amounts. What is more, the same user may act differently in different situations when different corrections are needed. For example, user USR may act more aggressively in terms or rotations, but may be slower and carful when shifting, or vice versa.

The machine learning approach in user guidance for imaging geometry adjustment as proposed herein is configured to take into account particular user habit characteristics of reacting to such instructions. If a certain user is given instructions not tailored to his or her habits, the same correction result may only be achieved after more time consuming iterations. But with the proposed machine learning model, the number of iteration adjustments can be reduced at least on average for a given user. This is because the output correction information computed by the machine learning module factors in the user peculiarities on reacting differently to spatial instructions for changing imaging geometries. The use of machine learning ("ML") models has been found to be of particular benefit to explore the relationships between types of correction information. This ML task can be conceptualized as a latent, unknown, functional relationship between (input) correction information as provided on purely geometrical grounds (such as provided by the navigation unit) and (output) correction information that represent adjustments performed by the user in response to instructions. Previously recorded training data is used to train the ML model to learn this relationship and to thus personalize the machine learning module to the particular preference of a specific user for adjustment purposes.

Unlike classical/analytical modelling approaches, the machine learning models do not generally require the designer to make specific assumptions on functional dependency types. For example, the above described relationship between input and output correction information is expected to be highly non-linear which would exclude any sort of linear models. Machine learning models have been found to be good at learning in particular such highly non-linear relationships. Parameters also referred to as "weights" of the machine learning model are adjusted in an optimization procedure to be described at FIG. 8 in more detail below to account for the training data. The totality of all parameters adjusted by the model then represents or encodes the said latent relationship.

If a sufficient amount of representative training data is available for a given user, the machine learning model can be personalized for the particular user. Indeed, it is proposed herein that each user of a group of users (such as clinicians in a radiological department) may be assigned their dedicated, separate machine learning model, each trained for each user respectively on personal training data collected for each user, respectively. The so "per-user-trained" models MLM1-4 may then be stored in a database MEM. The system SYS may include a user identification mechanism UID configured to identify each user upon presentation of user credentials. Once identified, the pre-trained machine learning module previously associated with the particular user is then accessed to compute the instructions personalized for that user.

Referring now briefly to the learning aspect this includes a training data collection phase or monitoring phase and training phase. Both can be a done as one-off operations, or can be repeated to refine the respective model as the user is using the imaging apparatus.

In the training data collection phase, actual imaging geometry adjustments performed by the user are recorded and stored in a memory MEM-T as training data. It is then the task in the monitoring phase to monitor the peculiar manners of each user and how they react to correction information and related instructions.

This training data collection phase may operate as follows. The user is identified by the user identification UID by providing a password, biometric input or other credential. At this stage during the monitoring or "user familiarization" phase, the correction information is provided by the neural-network as standard instructions, not yet based on personalized correction information. The monitoring is in effect during normal clinical use. At this stage the benefits of the proposed system are hence not yet felt. The correction information as provided by the navigation unit NU as the deviation between the current and target imaging geometry may be provided at this stage as standard correction information, suitably modulated by modulator MOD.

The mounting mechanism MM or the user input devices JS, such the joy-stick or other, may include preferably encoders ENC to track and record the actual user adjustments performed by the user in response to the standard instructions over the course of normal clinical use, during ward rounds for example. The tracked adjustments may be stored, for example in vector form, in association with the respective provided standard correction information/instruction as originally provided by the navigation unit. In this manner, pairs (x,y) of correction information are built: for each pair, the correction information "x" as provided by the navigation unit NU, and the correction information "y" based on the actual user adjustments as recorded by the encoders ENC in response to correction information x as provided. Over time, as the user USR uses the imaging device, a plurality of such pairs $(x_k, y_k)$ of correction information are recorded and stored in the training data memory MEM-T. Because of the provided use credentials, the collected training data pairs can be stored per user and can be later retrieved.

Once a sufficient number of such training pairs $(x_k, y_k)$ have been accumulated over usage time, which may take, depending on the frequency of usage a few days or weeks, the leaning phase may commence. Initially, an initialized model is set up, pre-populated with some random parameters. The initial model is assigned to the user based on the user credentials as collected by the user identification mechanism UID. The initialized model is accessed. The model has a certain architecture, such as artificial neural-network. The machine learning task for present purposes is in general one of regression where the input correction information is regressed into personalized imaging geometry correction information, referred to briefly as output correction information. As this type of data is non-image data, fully connected neural-networks may be preferred. However, nothing herein is restricted to neural-networks and other machine learning techniques may be used instead.

The learning phase may include the above mentioned optimization procedure to adjust the current set of parameters of the model. In the learning phase, a current or the initial set of parameters as present in the machine learning model is adjusted in light of the training data so far collected. High performance computing devices such as GPUs may be used as training system TS to quickly perform this optimization or learning algorithm. The optimization itself may be formed during the time the imager is out of use. Over time then, as the machine learning system collects more training data and after more runs of the training algorithm, the instructions provided will become more tailored to the user's specific habits and thus fewer iterations in general may be required to obtain the target geometry. This saves time, especially in busy clinical settings. More patients can be imaged over a given time period. Image throughput is increased.

Figure 6:
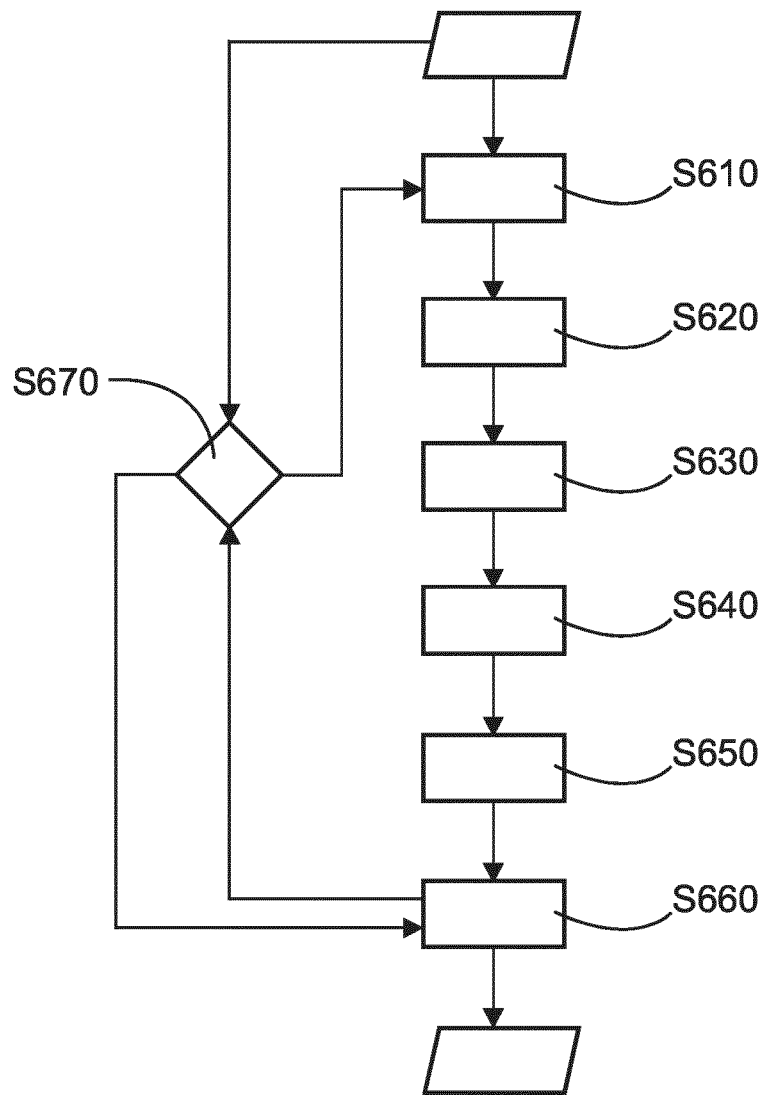
FIG. 6 shows a flow chart of a method of supporting X-ray imaging.

Reference is now made to FIG. 6 which is a flow chart of a method of supporting X-ray imaging. The method may underline operation of the above described system SYS, but it may also be understood that the method and its steps may also be understood as a teaching in their own right. The method is implemented on one or more suitable computing devices. In FIG. 6, it is assumed that the machine learning model has been sufficiently trained on previous usage data with the understanding that the learning phase may not necessarily be a one-off operation but may be done repeatedly once a new batch of training data has been collected. Training aspects will be explained in more detail below with reference to FIGS. 7-9.

At step S610 input data is received. The input data comprises in particular user credentials.

At step S620 the user is identified based on the user credentials. Steps S610 and 620 are optional.

At step S630 in a given imaging session administered by the user, first/input correction information is computed that quantifies a mismatch between a current imaging geometry and target geometry. In embodiments the step of computing the correction information is performed based on sensor readings or is performed on measurements obtained at the detector based on low dosage pre-shots as explained above in relation to any one of FIGS. 4,5.

At step S640 based on the first correction information, output personalized correction information is computed for the user by a pre-trained machine learning model as implemented by a machine learning module. The machine learning module is a computational arrangement that implements the machine learning model pre-trained on training data.

The pre-trained training data used includes in particular pairs of i) previous correction information as provided by navigation unit, and ii) imaging geometry adjustments performed by the user in response to instructions modulated from the previous correction information. Preferably, multiple such pairs have been recorded previously in a training data collection phase, at the conclusion of which the model was adapted by a learning algorithm based on the training data to better personalize the correction information provided by the machine learning model.

At step S650 the so computed personalized instructions are used to modulate a sensory signal discernable by the user to so convey to the user instructions on how to adjust the current imaging geometry.

The modulation may include modulating any one or more optical light beams or by delivering modulated mechanical vibrations through a manual actuator, user input device or other device which the user may contact during use to effect the imaging geometry adjustment. Light modulations may include modulations of any one or more of color, light intensity, hue or any combination thereof. In addition or instead, instructive light symbols are projected onto a surface such as on the patient's contours in the form of arrows, etc. In addition or instead, animations are shown that represent the instructions to be performed by the user.

At step S660 the modulated sensory signals are output to the user.

At step S670 an event handler or other is used to establish whether the current imaging geometry has been changed due to user adjustments. If yes, new correction information is computed and the above work flow is repeated. If it is established that no change of imaging geometry has occurred the currently displayed instructions are maintained at step S660.

In this way a dynamic feedback loop is realized that provides quasi-real time instruction updates, until the target geometry is achieved (within a pre-set error margin).

The personalized correction information as computed by the machine leaning model, and hence the personalized modulated instruction, are dynamically adapted in a manner in which the specific user tends to act on correction information, so as facilitate reducing the amount of iterations required to achieve the target geometry.

Figure 7:
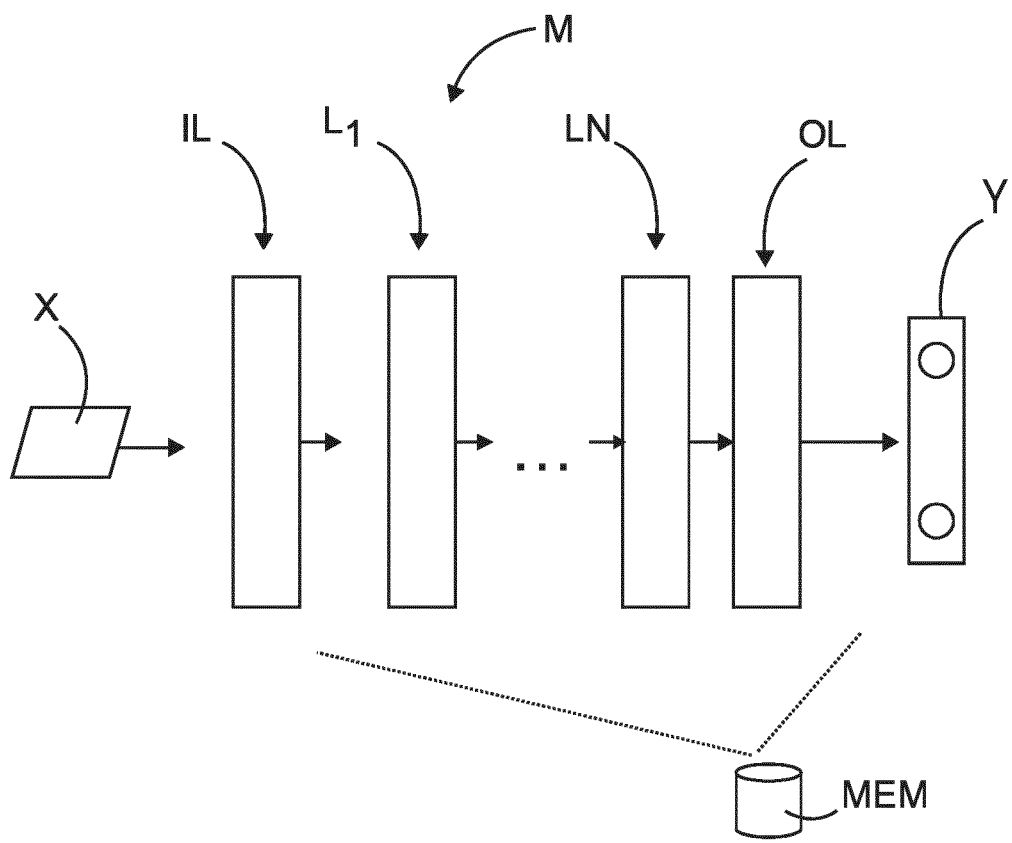
FIG. 7 shows a schematic block diagram of a machine learning model.

Reference is now made to FIG. 7 which shows a schematic diagram of a neural-network type model that may be used in embodiments. As mentioned earlier, the model may include one or more fully connected layers (as opposed as to layers in a convolutional network) that regress the input that is imaging adjustment instructions to personalized image instructions for a given user.

The model M may be trained by a computerized training systems TS to be described more fully below at FIG. 8. In training, the training system TS adapts an initial set of (model) parameters $\theta$ of the model M. In the context of neural network models, the parameters are sometime referred to herein as weights. The training data is collected in the monitoring phase as mentioned above. After the monitoring phase, two further processing phases may thus be defined in relation to the machine learning model NN: a training phase and a deployment (or inference) phase.

In training phase, prior to deployment phase, the model is trained by adapting its parameters based on the training data. Once trained, the model may be used in deployment phase to predict the personalized correction information. The training may be a one-off operation, or may be repeated once new training data become available.

The machine learning model M may be stored in one (or more) computer memories MEM'. The pre-trained model M may be deployed as a machine learning component MLM on a computing device PU, preferably integrated in the imager IA. Preferably, to achieve good throughput, the computing device PU includes one or more processors (CPU) that support parallel computing, such as those of multi-core design. In one embodiment, GPU(s) (graphical processing units) are used.

Referring now in more detail to FIG. 7, this shows a neural network M in feed-forward architecture. The network M comprises a plurality of computational nodes arranged in layers $L_1$-$L_N$ in a cascaded fashion, with data flow proceeding from left to right and thus from layer to layer. Recurrent networks are not excluded herein.

In deployment, the input data x is applied to input layer IL, such as x=a correction information as supplied by the navigation unit NU. The input data x then propagates through a sequence of hidden layers $L_1$-$L_N$ (only two are shown, but there may be merely one or more than two), to then emerge at an output layer OL as an estimated output M(x), the personalized correction information. The output can be modulated into personalized instructions by modulator MOD as described above.

The model network M may be said to have a deep architecture because it has more than one hidden layers. In a feed-forward network, the "depth" is the number of hidden layers between input layer IL and output layer OL, whilst in recurrent networks the depth is the number of hidden layers, times the number of passes.

The layers of the network, and indeed the input and output imagery, and the input and output between hidden layers (referred to herein as feature maps), can be represented as two or higher dimensional matrices ("tensors") for computational and memory allocation efficiency. The dimension and the number of entries represent the above mentioned size.

Preferably, the hidden layers $L_1$-$L_N$ include one or more convolutional layers but are preferably exclusively fully connected layers. The number of layers is at least one, such as 2-5, or any other number. The number may run into double-digit figures.

Fully connected layers FC are beneficial in regression tasks of non-image as is the case herein for the processing of correction information. However, one or more convolutional layers may still be used in embodiments.

A fully connected layer is distinguished from a convolutional layer in that an entry in the output feature map of a fully connected layer is a combination of all nodes received as input from a previous layer by that layer. In other words, a convolutional layer is only applied, per feature map entry, to sub-sets of the input as received from an earlier layer.

The correction information as applied as input X to the input layer may be presented as vector (s,φ,d) to represent a point in phase PS as described in FIG. 2B above. The output Y, the personalized correction information, may likewise be represented as one or more vectors in phase space but may differ in general from the input. The output may be represented by more than one vector $(s_j,φ_j,d_j)^j$, for example as matrix or tensor. The output Y may represent one or more different correction paths pa in phase space as described in relation to FIG. 2B to better represent the user preferred adjustments. If the output is a matrix to represent a more complex correction path, this would appear, on the face of it, to introduce a more complicated correction information that, one may argue, cause the user to apply the instructions in multiple iterations still. However, this complication is only apparent. Whilst the correction information Y as output by the ML model M may appear more complex for certain users, it is still personalized to the user and easier to interpret and put into practice by the specific user. The possibly more complex output correction information Y does better conform to the manual dexterity level of the user. The upshot is that fewer iterations are on average still required, as compared to a seemingly simpler standard instruction that the user nevertheless may find harder to implement.

The representation of the correction information as vector or matrices may sometimes lead to sparseness in representation which may be undesirable. Embedding techniques may be used to encode the correction information data into a more useful, "denser", representation which can then be better processed by the network model. Such embeddings may include for example one-hot encoding schemes. In other embodiments, an auto-encoder setup is used to process the correction information (the input X) data first into a suitable representation, a "code", and it is this code which is then fed into the actual model M to be trained. In other words, a separate machine learning step may be used for pre-processing the data.

It will be understood that the above described model M in FIG. 7 is merely according to one embodiment and is not limiting to the present disclosure. Other neural network architectures are also envisaged herein with more or less or different functionalities than describe herein, such as pooling layers or drop-out layers or others still. What is more, models M envisaged herein are not necessarily of the neural network type at all. Other, classical statistical regression methods based on sampling from training data are also envisaged herein in alternative embodiments. Still other techniques may include Bayesian networks, or random fields, such as Markov type random field and others.

Figure 8:
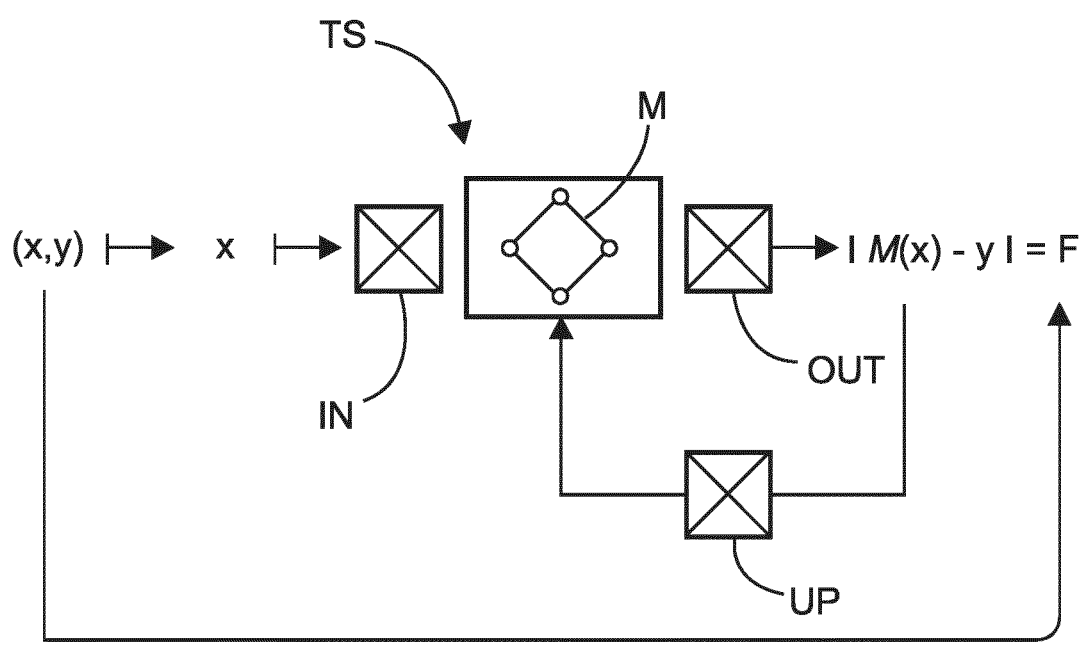
FIG. 8 shows a training system for training a machine learning model.

Reference is now made to FIG. 8 which shows a training system TS to train a machine learning module In more detail, FIG. 8 which shows a training system TS for training the parameters, i.e. the weights of a machine learning model M, such as in a neural network as discussed in FIG. 7, or other neural network-type model, or indeed non-neural network type ML models.

The training data comprises k pairs of data $(x_k, y_k)$. k may run into the 100s or 1000s for example. The training data comprises for each pair, training input data $x_k$ and an associated target $y_k$. The training data is thus organized in k pairs, in particular for supervised learning schemes as mainly envisaged herein. However, it should be noted that non-supervised learning schemes are not excluded herein.

The training input data $x_k$ comprises the standard input correction information $x_k$ provided in during regular clinical use in the monitoring phase. The associated target $y_k$ or "ground truth" is the actual adjustments (output correction information) $y_k$ as performed by the user in response to the input correction information. The pairs $(x_k, y_k)$ are recorded in training data memory MEM-T during the above described monitoring phase. Again, each member $x_k$, $y_k$ of may be presented as vectors as points or paths in phase space as described above in FIG. 2B and FIG. 7.

The model is of the regression type and attempts to regresses $x_k$ into $y_k$ as will be explained in more detail. In the training phase, an architecture of a machine learning model M, such as the shown artificial neural network ("NN") in FIG. 7 is pre-populated with initial set of weights. The weights θ of the model M represent a parameterization $M^θ$, and it is the object of the training system TS to optimize and hence adapt the parameters θ based on the training data $(x_k, y_k)$ pairs. In other words, the learning can be formulated mathematically as an optimization scheme where a cost function F is minimized although the dual formulation of maximizing a utility function may be used instead.

Assuming for now the paradigm of a cost function F, this measures the aggregated residue(s), that is, the error incurred between data estimated by the neural network model NN and the targets as per some or all of the training data pairs k:

$$\text{argmin } _θ F = Σ_k \|M^θ(x_k) - Y\| \quad (2)$$

In eq. (2) and below, function M(denotes the result of the model NN applied to input x. The cost function may be pixel/voxel-based, such as the L1 or L2-norm cost function. In training, the training input data $x_k$ of a training pair is propagated through the initialized network M. Specifically, the training input $x_k$ for a k-th pair is received at an input IL, passed through the model and is then output at output OL as output training data $M^θ(x)$. A suitable measure ||a??|| is used such as a p-norm, squared differences, or other, to measure the difference, also referred to herein as residue, between the actual training output $M^θ(x_k)$ produced by the model M, and the desired target $y_k$.

The output training data $M(x_k)$ is an estimate for target $y_k$ associated with the applied input training image data $x_k$. In general, there is an error between this output $M(x_k)$ and the associated target $y_k$ of the presently considered k-th pair. An optimization scheme such as backward/forward propagation or other gradient based methods may then be used to adapt the parameters θ of the model M so as to decrease the residue for the considered pair $(x_k, y_k)$ or a subset of training pairs from the full training data set.

After one or more iterations in a first, inner, loop in which the parameters θ of the model are updated by updater UP for the current pair $(x_k, y_k)$, the training system TS enters a second, an outer, loop where a next training data pair $x^{k+1}, y^{k+1}$ is processed accordingly. The structure of updater UP depends on the optimization scheme used. For example, the inner loop as administered by updater UP may be implemented by one or more forward and backward passes in a forward/backpropagation algorithm. While adapting the parameters, the aggregated, for example summed, residues of all the training pairs are considered up to the current pair, to improve the objective function. The aggregated residue can be formed by configuring the objective function F as a sum of squared residues such as in eq. (2) of some or all considered residues for each pair. Other algebraic combinations instead of sums of squares are also envisaged.

Optionally, one or more batch normalization operators ("BN", not shown) may be used. The batch normalization operators may be integrated into the model M, for example coupled to one or more of the convolutional operator CV in a layer. BN operators allow mitigating vanishing gradient effects, the gradual reduction of gradient magnitude in the repeated forward and backward passes experienced during gradient-based learning algorithms in the learning phase of the model M. The batch normalization operators BN may be used in training, but may also be used in deployment.

The training system as shown in FIG. 8 can be considered for all learning schemes, in particular supervised schemes. Unsupervised learning schemes may also be envisaged herein in alternative embodiments. GPUs may be used to implement the training system TS.

The fully trained machine learning module M may be stored in one or more memories MEM or databases. The training is performed per user, to obtain different pre-trained model for each user as discussed above.

Figure 9:
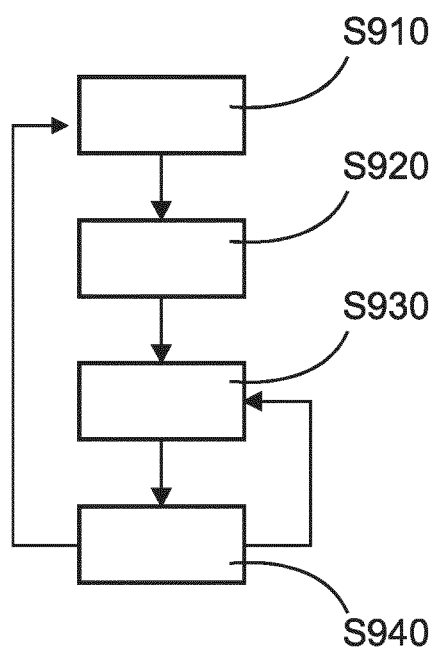
FIG. 9 shows a method for training a machine learning model.

FIG. 9 is a flow chart of a method of training a machine learning model such as the one described in any one of the above described embodiments.

Suitable training data needs to be collected as described above in the monitoring phase. Preferably, supervised learning schemes are envisaged herein although this is not a necessity as unsupervised learning setups are also envisaged herein.

In supervised learning, the training data includes suitable pairs of data items, each pair including training input data and associated therewith a target training output data. Specifically, the training data pairs $(x_k, y_k)$ are as described above and as collected during the monitoring phase and stored in training data memory MEM-T.

With continued reference to FIG. 9, at step S910 training data is received in the form of pairs $(x_k, y_k)$. Each pair includes the training input $x_k$ and the associated target $y_k$. $x_k$, as defined in FIG. 8 above.

At step S910 training input is received.

At step S920, the training input $x_k$ is applied to an initialized machine learning model NN to produce a training output.

At step S930 a deviation, or residue, of the training output $M(x_k)$ from the associated target $y_k$ is quantified by a cost function F. One or more parameters of the model are adapted at step S940 in one or more iterations in an inner loop to improve the cost function. For instance, the model parameters are adapted to decrease residues as measured by the cost function. The parameters include in particular weights W of the convolutional operators, in case a convolutional NN model M is used.

The training method then returns in an outer loop to step S910 where the next pair of training data is fed in. In step S920, the parameters of the model are adapted so that the aggregated residues of all pairs considered are decreased, in particular minimized. The cost function quantifies the aggregated residues. Forward- backward propagation or similar gradient-based techniques may be used in the inner loop S930-S940.

More generally, the parameters of the model M are adjusted to improve objective function F which is either a cost function or a utility function. In embodiments, the cost function is configured to the measure the aggregated residues. In embodiments the aggregation of residues is implemented by summation over all or some residues for all pairs considered. The method may be implemented on one or more general-purpose processing units TS, preferably having processors capable for parallel processing to speed up the training.

The components of the training system TS may be implemented as one or more software modules, run on one or more processing computing systems, preferably having high performance processors, such as GPU. The training is preferably not performed by the processing unit PU of the imager IA, but may be done externally by a more powerful computing system such as one or more servers. Once trained, the model can be loaded into a data storage MEM of the imager's IA own computing system PU. The data storage MEM may hold the models MLM1-4 for multiple users. The model associated with a given user is accessed upon identification of the user by the user identification system UID as explained above.

Whilst main reference to the imaging of human patients in the medical field has been made herein, the principles disclosed herein may be used to image instead animals, pets, on farms for instance. In addition, imaging of objects is also envisaged, such as in baggage screening or non-destructive material testing, in scenarios where a level of mobility/portability is required.

The methods or components of the system SYS may be implemented as one or more software modules, run on one or more general-purpose processing units PU such as a workstation associated with the imager IA, or on a server computer associated with a group of imagers.

Alternatively, the methods or some or all components of the system SYS may be arranged in hardware such as a suitably programmed microcontroller or microprocessor, such an FPGA (field-programmable-gate-array) or as a hard-wired IC chip, an application specific integrated circuitry (ASIC), integrated into the imager IA. In a further embodiment still, the system SYS may be implemented in both, partly in software and partly in hardware.

The step of the methods or different components of the system SYS may be implemented on a single data processing unit PU. Alternatively, some or all components or the method steps may be implemented on different processing units PU, possibly remotely arranged in a distributed architecture and connectable in a suitable communication network such as in a cloud setting or client-server setup, etc.

One or more features described herein can be configured or implemented as or with circuitry encoded within a computer-readable medium, and/or combinations thereof. Circuitry may include discrete and/or integrated circuitry, a system-on-a-chip (SOC), and combinations thereof, a machine, a computer system, a processor and memory, a computer program.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium (in particular, but not necessarily, a non-transitory medium), such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A system for controlling X-ray imaging, comprising:
    a memory for storing a plurality of instructions comprising a pre-trained machine learning model; and
    an X-ray imaging apparatus comprising an X-ray source, an X-ray detector with no rigid mechanical coupling between the X-ray source and the X-ray detector, and controller circuitry;
    wherein a processor is coupled to the memory and configured to execute the pre-trained machine learning model to compute output correction information for adjusting an imaging geometry of the X-ray imaging apparatus to achieve a target imaging geometry, wherein the controller circuitry is configured to provide a user instruction for the imaging geometry adjustment, modulated based on the output correction information, and wherein the processor is configured to execute the pre-trained machine learning model previously trained on training data including specific user's responses to previous user instructions for imaging geometry adjustments, and wherein multiple pre-trained or trainable machine learning models are associated with different users.

2. The system according to claim 1, further comprising a user identification functionality configured to identify a user based on a credential and to cause selection of the machine learning model from the multiple pre-trained or trainable machine learning models based on the credential.

3. The system according to claim 1, wherein:
    the controller circuitry is configured to control a visible light projector to project a light beam onto a surface, the light beam modulated in accordance with the output correction information, and/or
    the controller circuitry is configured to control a haptic vibrator to impart on a) a manual actuator mechanically coupled to the X-ray source of the X-ray imaging apparatus or b) on an electrical input communicatively coupled to the X-ray source of the X-ray imaging apparatus, mechanical vibrations being in accordance with the output correction information, and/or
    the controller circuitry is configured to control an electroacoustic transducer to sound out the user instruction in accordance with the output correction information.

4. The system according to claim 1, wherein, upon a change of a current imaging geometry, the user instruction is updated.

5. The system according to claim 1, comprising a navigation unit configured to compute input correction information based on which the output correction information is computed by the machine learning model, the input correction information computed based on one of:
    i) sensor readings provided by sensors arranged at the X-ray imaging apparatus;
    ii) a scout image acquired using a collimator setting to effect a projection being detected at the X-ray detector of the X-ray imaging apparatus, the projection having a shape, the input correction information being computed based on a distortion of the shape relative to a pre-determined reference shape; and
    iii) an intensity profile as detected at the X-ray detector and caused by an anti-scatter grid.

6. The system according to claim 3, wherein modulation of light by the controller circuitry includes at least one of: a change of a light pattern cast by the light beam, a change in light gradient, and a change in light color and/or hue.

7. The system according to claim 3, wherein the surface is in an examination region of the X-ray imaging apparatus.

8. The system according to claim 7, wherein the surface is defined by a patient when present in the examination region.

9. A method for controlling X-ray imaging, comprising:
    computing, by a processor configured to execute a pre-trained machine learning model, output correction information for adjusting an imaging geometry of an X-ray imaging apparatus, wherein the X-ray imaging apparatus is of the mobile type comprising an X-ray source and an X-ray detector with no rigid mechanical coupling between the X-ray source and the X-ray detector, to achieve a target imaging geometry, and providing, by controller circuitry, a user instruction for imaging geometry adjustment, modulated based on the output correction information, wherein the processor is configured to execute the pre-trained machine learning model is previously trained on training data including specific user's responses to previous user instructions for imaging geometry adjustments, and wherein multiple pre-trained or trainable machine learning models are associated with different users.

10. A non-transitory computer readable medium having stored thereon executable instructions which, when executed by at least one processor, cause the at least one processor to perform a method for controlling X-ray imaging, the method comprising:

computing, by a processor configured to execute a pre-trained machine learning model, output correction information for adjusting an imaging geometry of an X-ray imaging apparatus, wherein the X-ray imaging apparatus is of the mobile type comprising an X-ray source and an X-ray detector with no rigid mechanical coupling between the X-ray source and the X-ray detector, to achieve a target imaging geometry, and providing, by controller circuitry, a user instruction for imaging geometry adjustment, modulated based on the output correction information, wherein the processor is configured to execute the pre-trained machine learning model previously trained on training data including specific user's responses to previous user instructions for imaging geometry adjustments, and wherein multiple pre-trained or trainable machine learning models are associated with different users.

* * * * *